United States Patent
Campora (10) Patent No.: US 11,253,565 B2
(45) Date of Patent: Feb. 22, 2022

(54) NANOPARTICLE OPHTHALMIC COMPOSITION FOR THE TREATMENT OF OCULAR DISORDERS OR DISEASES

(71) Applicant: Eye Pharma S.p.A., Genoa (IT)

(72) Inventor: Giuseppe Campora, Ruta di Camogli (IT)

(73) Assignee: EYE PHARMA S.P.A., Genoa (IT)

( * ) Notice: Subject to any disclaimer, the term of this patent is extended or adjusted under 35 U.S.C. 154(b) by 127 days.

(21) Appl. No.: 16/118,571

(22) Filed: Aug. 31, 2018

(65) Prior Publication Data

US 2019/0070242 A1    Mar. 7, 2019

(30) Foreign Application Priority Data

Sep. 5, 2017   (IT) .......... 102017000099156

(51) Int. Cl.
| | | |
|---|---|---|
| *A61K 36/535* | (2006.01) | |
| *A61K 9/51* | (2006.01) | |
| *A61K 31/728* | (2006.01) | |
| *A61P 27/04* | (2006.01) | |
| *A61K 47/36* | (2006.01) | |
| *A61K 9/00* | (2006.01) | |
| *A61K 47/46* | (2006.01) | |

(52) U.S. Cl.
CPC .......... *A61K 36/535* (2013.01); *A61K 9/0048* (2013.01); *A61K 9/51* (2013.01); *A61K 9/5123* (2013.01); *A61K 31/728* (2013.01); *A61K 47/36* (2013.01); *A61K 47/46* (2013.01); *A61P 27/04* (2018.01)

(58) Field of Classification Search
None
See application file for complete search history.

(56) References Cited

U.S. PATENT DOCUMENTS 5,512,329 A * 4/1996 Guire et al.
2010/0305045 A1 * 12/2010 Yu et al.

FOREIGN PATENT DOCUMENTS

| DE | 202014010412 U1 | 9/2015 |
|---|---|---|
| WO | 2012090170 A1 | 7/2012 |
| WO | WO 2012090170 A1 * | 7/2012 |

OTHER PUBLICATIONS

Italian Search Report for Corresponding Italian Application No. 201700099156 (2 Pages) (dated Apr. 30, 2018).
Sergio C. Sacca, et al., "Protection of Trabecular Meshwork Cells By Eyedrops Containing High Concentration of Polyphenols", New Frontiers in Ophthalmology, vol. 5, pp. 1-7, 2019.

* cited by examiner

*Primary Examiner* — Dominic Lazaro
(74) *Attorney, Agent, or Firm* — Lucas & Mercanti, LLP (57) ABSTRACT

Is herein described a nanoparticle ophthalmic composition comprising at least 0.1% of *Perilla frutescens* extract and at least 0.1% of hyaluronic acid or a salt thereof wherein the *Perilla frutescens* extract has a content of polyphenols of at least 2.5% by weight of the total weight of the extract and to the use of said ophthalmic composition in the treatment of ocular disorders or diseases such as tear dysfunction syndrome, dry eye, diabetic retinopathy and glaucoma, preferably in the treatment of tear dysfunction syndrome.

15 Claims, 9 Drawing Sheets

NANOPARTICLE OPHTHALMIC COMPOSITION FOR THE TREATMENT OF OCULAR DISORDERS OR DISEASES

CROSS-REFERENCE TO RELATED APPLICATIONS

This application claims the benefit of priority from Italian Patent Application 102017000099156, filed Sep. 5, 2017, the contents of which are incorporated herein by reference.

FIELD OF THE INVENTION

The present invention refers to a nanoparticle ophthalmic composition comprising at least 0.1% of *Perilla frutescens* extract and at least 0.1% of hyaluronic acid or a salt thereof. Said composition is particularly useful in the treatment of ocular diseases or disorders such as for example tear dysfunction syndrome, dry eye, diabetic retinopathy and glaucoma, preferably in the treatment of tear dysfunction syndrome.

Background of the Invention

As known, tear dysfunction syndrome (also known as dry eye) is a multifactorial disease which causes impaired vision, instability of the tear film associated with an increase in the osmolarity thereof and inflammation of the ocular surface.

The percentage of this disease increases with age and involves ocular surface and tear film structures.

Said disease manifests itself with symptoms such as discomfort, burning, photophobia, foreign-body sensation and pain affecting work activity and life quality of those affected.

The integrity of the ocular surface is maintained by a stable pre-ocular tear film.

Behind lacrimal dysfunctions there is the presence of an instable tear film due to an improper amount, diffusion and quantity of the different components of tears. In particular, two types of tear dysfunction syndrome have been identified: due to a reduced tears production by the gland (hyposecretory) and due to an increased loss of the aqueous portion following evaporation (hyperevaporative).

Ocular irritation and suffering of the structures of the ocular surface due to the tear film malfunction persisting in time lead to an inflammatory state of dryness-inflammation-dryness, which tends to auto-maintain itself establishing a vicious cycle.

Since inflammation is a key feature of the pathogenesis of the ocular surface dysfunction, the therapeutic approach is often multiple in order to try to reduce the inflammatory state, restore the functionality of Meibomian glands and normalize the osmolarity of the aqueous film.

As regards glaucoma, said ocular disease affects the optical nerve and generally is due to a progressive increase of the intraocular pressure. In the eye affected by glaucoma, the aqueous humor outflow is impeded. In several forms of glaucoma, trabecular meshwork cells are damaged as a result of oxidative stress deriving from the environment, vascular dysregulation, ageing and/or pathogenic processes.

Epidemiological evidences show that conditions of environmental oxidative stress, ocular surgeries, use of systemic drugs or eye drops and ophthalmic creams for unappropriated times and formulation are able to induce conditions of ocular imbalance, fostering the onset of tear dysfunction syndrome or some forms of glaucoma.

Moreover several products, particularly eye drops or ophthalmic creams, commercially available or known in the art for the treatment of ocular diseases or disorders, such as tear dysfunction syndrome, dry eye or glaucoma, show a good lubricant and moisturizing activity, but poor anti-inflammatory and antioxidant activity or they poorly penetrate in the anterior chamber of the eye or, again, demonstrate poor permanence of the active ingredient at ocular level and therefore present poor corneal bioavailability and therapeutic efficacy.

In addition, highly effective and secure ophthalmic compositions comprising natural components for the treatment of eye diseases or disorders are more and more requested.

In order to partially overcome these drawbacks, ophthalmic compositions comprising a *Perilla* extract and hyaluronic acid for the treatment of ocular diseases and disorders have been studied and described in the art (see for example WO 2012/090170). Said compositions have been shown to have a good anti-inflammatory and antioxidant activity at ocular level.

As known, *Perilla* and in particular *Perilla frutescens* is an annual herbaceous plant of the Lamiacee family native to eastern Asia. A multitude of studies in literature demonstrate the anti-inflammatory, antiallergenic and antioxidant activity of said medicinal plant.

In particular, *Perilla frutescens* extracts, such as for example the dry hydroalcoholic extract, contain fatty acids such as myristic, palmitic, α and γ linolenic acid, linoleic acid, oleic acid, stearic acid, catechins and polyphenols such as the rosmarinic acid, luteolin, caffeic acid, apigenin, ferulic acid, chrysoeriol. In particular, luteolin is a flavone with known anti-inflammatory and anti-allergic activity.

The parts of *Perilla frutescens* containing the most amount of polyphenols are the leaves and the seeds, therefore, to obtain *Perilla frutescens* extracts, said parts of the plant are used.

Hyaluronic acid is a naturally occurring, either of animal or vegetal origin, non-sulphated glycosaminoglycan that presents several properties, among which moisturizing and moistening properties.

In any case, the ophthalmic compositions known in the art comprising *Perilla frutescens* extracts and hyaluronic acid, despite having a good anti-inflammatory and antioxidant activity at ocular level, do not show sufficient ocular permeation and permanence abilities such as to result in an optimum efficacy for the treatment of ocular disorders and diseases, such as in particular tear dysfunction syndrome, dry eye and glaucoma.

Therefore, there is an increasing need of novel ophthalmic compositions for the treatment of ocular diseases and disorders, such as for example tear dysfunction syndrome, dry eye, diabetic retinopathy and glaucoma, comprising a *Perilla frutescens* extract and hyaluronic acid which overcome the drawbacks of ophthalmic compositions comprising a *Perilla frutescens* extract and hyaluronic known in the art.

SUMMARY OF THE INVENTION

The invention includes a surprisingly found nanoparticle ophthalmic composition having an optimum lubricant, wetting, anti-inflammatory, antioxidant activity and, at the same time, better ocular penetration and permanence ability which comprises a specific amount of a *Perilla frutescens* extract and hyaluronic acid or a salt thereof. Said nanoparticle ophthalmic composition according to the present invention is also safe and particularly stable.

Therefore, an object of the present invention is a nanoparticle ophthalmic composition comprising:
- at least about 0.1% by weight of a *Perilla frutescens* extract;
- at least about 0.1% by weight of hyaluronic acid or a salt thereof;

wherein the *Perilla frutescens* extract has a content of polyphenols of at least 2.5% by weight of the total weight of the extract.

With the term "polyphenols" are meant substances of plant origin with phenolic structure, in particular flavonoids, such as quercetin, apigenin, hesperidin, hesperetin, luteolin, epigallocatechin gallate, epicatechin gallate, rutin, naringenin, myricetin, chrysine, eriodictyol and kaempferol.

With the term "ophthalmic composition" according to the present invention is meant a pharmaceutical composition suitable for ocular administration.

In particular, an ophthalmic composition according to the present invention can be a liquid sterile formulation, preferably eye drops, provided in single-dose or multidose containers or a semisolid formulation such as a cream or a gel.

The liquid sterile formulation can be an aqueous sterile solution or suspension, preferably an aqueous sterile solution.

The pH of the liquid sterile formulation is a pH tolerable at ocular level, typically a neutral pH namely between about 7 and about 7.4.

In order to maintain the pH of the liquid sterile formulation constant, a buffer system such as for example anhydrous sodium phosphate bibasic and sodium phosphate monobasic monohydrate can be added to the formulation.

The liquid sterile formulation according to the present invention has a viscosity between about 10 cSt (centistokes) and about 40 cSt.

Moreover, in order to maintain the characteristics of the liquid sterile formulation of the present invention optionally at least a thickener, such as for example sodium chloride, and at least a stabilizer can be further added.

The ophthalmic composition of the present invention in the form of a cream can be an ointment or a hydrophilic or lipophilic cream.

In a particularly preferred aspect of the present invention, the ophthalmic composition is an aqueous sterile solution in the form of eye drops.

*Perilla frutescens* extract according to the present invention means an aqueous, alcoholic, hydroalcoholic, glyceric or glycolic extract from leaves and seeds of *Perilla frutescens*. Moreover, the extract can be fluid, soft or dry.

In a particularly preferred aspect of the invention the *Perilla frutescens* extract is a dry hydroalcoholic extract.

The percentages as described according to the present invention are meant by weight with respect to the total weight of the composition, unless otherwise defined. Preferably, the ophthalmic composition according to the present invention comprises from about 0.1% to about 5%, more preferably from about 0.1% to about 0.2% and still more preferably about 0.10% or about 0.15% by weight of a *Perilla frutescens* extract, as previously defined, with respect to the total weight of the ophthalmic composition.

A hyaluronic acid salt according to the present invention can be for example sodium hyaluronate.

In a preferred aspect of the invention the ophthalmic composition of the present invention comprises sodium hyaluronate.

Preferably, the ophthalmic composition according to the present invention comprises about 0.1% to about 0.5%, more preferably 0.25% by weight of hyaluronic acid or a salt thereof of the total weight of the ophthalmic composition.

The composition of the present invention is a nanoparticle composition.

With the term "nanoparticles" are meant lipid particles, such as liposomes or micelles. Said nanoparticles are known in the art as carriers of pharmaceutical active ingredients [see for example Pulliero et al., *Carcinogenesis*, 36(3):368-77 (2015)].

The medium diameter of the nanoparticles is between about 50 and about 1000 nm and preferably is of about 100-500 nm, more preferably of about 60-80 nm, still more preferably of about 70 nm.

In another embodiment, the medium diameter of the nanoparticles is between about 50 and about 1000 nm and preferably is of about 100-500 nm, more preferably of about 40-60 nm, still more preferably of about 45-50 nm.

In a preferred embodiment, the medium diameter of the nanoparticles is of about 47. Preferably the nanoparticles used for the composition of the present invention are liposomal nanoparticles.

In a particularly preferred aspect of the invention the ophthalmic composition is a nanoparticle eye drops comprising:
- 0.10% or 0.15% by weight of *Perilla frutescens* extract;
- 0.25% of hyaluronic acid or a salt thereof, as previously defined;

wherein the *Perilla frutescens* extract has a content of polyphenols of at least 2.5% by weight of the total weight of the extract.

In the present contest, an eye drops comprising 0.10% by weight of a *Perilla frutescens* extract, 0.25% of hyaluronic acid or a salt thereof and water wherein the *Perilla frutescens* extract has a content of polyphenols of at least 2.5% by weight with respect to the total weight of the extract was defined standard concentration eye drops (for the sake of brevity standard eye drops or std eye drops). Instead, an eye drops comprising 0.15% by weight of a *Perilla frutescens* extract, 0.25% of hyaluronic acid or a salt thereof and water wherein the *Perilla frutescens* extract has a content of polyphenols of at least 2.5% by weight of the total weight of the extract was defined high concentration eye drops (for the sake of brevity high eye drops).

The *Perilla frutescens* extract employed in the compositions object of the present invention comprises, in addition to polyphenols, also carotenoids, catechins and fatty acids. In particular fatty acids are polyunsaturated acids such as myristic acid, palmitic acid, α-linoleic acid, γ-linoleic acid, linoleic acid, oleic acid and stearic acid. In a particularly preferred aspect, the eye drops object of the present invention can have the following composition (8 µg/mL nanoparticle concentration):

| COMPONENT | PERCENTAGE IN THE FORMULATION | FUNCTION |
| --- | --- | --- |
| PERILLA DRY EXTRACT TITRATED TO 2.5% IN POLYPHENOLS | 0.1-0.15% | ANTIOXIDANT |
| SODIUM HYALURONATE | 0.25% | MOISTURIZER |
| SODIUM CHLORIDE | Q.S. TO OSMOLALITY | OSMOLALITY CONTROL |
| SODIUM PHOSPHATE DIBASIC ANHYDROUS | Q.S. TO PH | BUFFER |
| SODIUM PHOSPHATE MONOBASIC MONOHYDRATED | Q.S. TO PH | BUFFER |
| PURIFIED WATER | Q.S. TO 100% | VEICHLE-DILUENT |

The starting material sodium hyaluronate present in the formulation is of biotechnological/fermentative origin. It appears in the form of a white powder or grains. It has a titre between 95 and 103.3%. A 0.5% solution thereof has a pH between 6.0 and 7.5. It contains a percentage of hyaluronic acid (HA) between 46.0 and 50.0% s/s, whereas the maximum protein content is equal to 0.1% s/s. The molecular weight ranges from 1.5 to 1.7 MDa.

The ophthalmic compositions as sterile liquid formulations according to the present invention can be prepared according to methods of pharmaceutical technique and technology known in the art.

In particular, a nanoparticle eye drops according to the present invention can be prepared through a process comprising:
a) preparation of an aqueous sterile solution comprising at least about 0.1% by weight of a *Perilla frutescens* extract, at least about 0.1% by weight of hyaluronic acid or a salt thereof wherein the *Perilla frutescens* extract has a content of polyphenols of at least 2.5% by weight of the total weight of the extract;
b) inclusion of the aqueous sterile solution in a nanoparticle carrier, preferably liposomes, to afford sterile nanoparticle eye drops.

The preparation of an aqueous sterile solution of step a) can be carried out using sterile components (excipients and active ingredients) and mixing them in sterile containers, in specifically arranged rooms for example equipped with laminar flow hoods.

The *Perilla frutescens* extract employed can be obtained from the leaves and/or seeds of the plant by extracting the plant in a mixture ethanol/water with a ratio of about 70:30.

The inclusion of the aqueous sterile solution of step b) can be obtained incubating the aqueous solution of step a) with nanoparticles, preferably liposomal, for some minutes, for example at room temperature for 15 minutes.

In a particularly preferred aspect, liposomes are prepared by adding a lipid mixture of 1,2-di-O-octadecenyl-3-trimethylammonium propane (chloride salt):cholesterol:D-alpha-tocopheryl polyethylene glycol 1000 succinate=49.5: 49.5:1 (molar ratio) in ethanol to a N-2-hydroxyethylpiperazine-N'-2-ethanesulfonic acid buffer (pH 7.4).

Preferably the eye drops thus obtained can be packaged in suitable single- or multi-use containers.

If the eye drops according to the present invention also comprise further excipients as previously defined, they are typically added in step a) of the above reported process.

A further object of the present invention is a process for preparing an eye drops as defined above.

As regards the sterile semisolid formulations according to the present invention such as creams, ointments and gels, they can be prepared by means of techniques known in pharmaceutical technique and technology.

Surprisingly the nanoparticle ophthalmic composition of the present invention, in particular in the form of eye drops, has proved to be particularly effective in the treatment of ocular disorders or diseases and particularly in the treatment of the tear dysfunction syndrome, dry eye, diabetic retinopathy and glaucoma.

In fact, it has been found that a nanoparticle ophthalmic composition according to the present invention, preferably in the form of eye drops, is able to stop the oxidative damage induced in vitro in sclerocorneal trabecular meshwork cells, to stop the oxidative damage induced in samples of sclerocorneal trabecular meshwork collected ex-vivo from donors of cornea and patients affected by glaucoma undergoing therapeutic trabeculectomy surgery and shows better ocular permanence, penetration and bioavailability besides optimal moistening, moisturising, anti-inflammatory and antioxidant properties. Moreover, the composition according to the present invention has also shown to be safe and stable from a chemical-physical point of view.

Therefore, a further object of the present invention is an ophthalmic composition as previously defined for use in the treatment of ocular disorders and diseases, preferably tear dysfunction syndrome, dry eye, diabetic retinopathy and glaucoma. The methods of treatment can be carried out by administering a therapeutically effective amount of an ophthalmic composition as described herein to an affected region of the eye of a patient requiring such treatment. The compositions are preferably administered topically to the eye or affected region thereof. For example, in one aspect of the invention, the composition is in the form of eye drops and the treatment can be carried out by instilling, for example, about one (1) or three (3) drops into the affected eye(s) of the patient as needed, one or more times a day.

DETAILED DESCRIPTION OF THE INVENTION

The objects and embodiments of the present invention will be illustrated in the following examples, which are for illustrative purpose only and are not meant to limit the scope of the invention.

Example

Lipid Nanoparticle Preparation

A lipid mixture was prepared by injecting 82.98 μL of 1,2-di-O-octadecenyl-3-trimethylammonium propane (DOTMA chloride salt), 47.85 μL of cholesterol and 3.78 μL of d-Alphatocopheryl polyethylene glycol 1000 succinate (TPGS) at a 49.5:49.5:1 molar ratio in ethanol (134.61 μL) till a final concentration of 10 mg/mL.

Then 900 μL of N-2-hydroxyethylpiperazine-N'-2-ethanesulfonic acid (HEPES) buffer (20 mM; pH=7.4), filtrated through a 0.22 μm filter, were added in a sterilized glass tube and the mixture was stirred on a vortex mixer. While stirring, 100 μL of lipid mixture were quickly injected using a needle into the HEPES buffer. The mixture was maintained under stirring for another 30 seconds and then sonicated in a sonication water bath for 10 minutes. The empty lipid nanoparticles (1 mg/mL) had a mean diameter of 46.82 nm.

It is worth noting that the concentration of the lipid mixture can be scaled up to 50 mg/mL to afford 5 mg/mL empty lipid nanoparticles.

The nanoparticles thus obtained were then incubated at room temperature with the eye drops, according to the present invention, for 15 minutes.

In Vitro Studies

Commercially available endothelial cellular lines of sclerocorneal trabecular meshwork were used. Said lines undergone a physiological ageing lasted about 10 cycles of cellular replication, thus representing a validated in vitro model of sclerocorneal trabecular meshwork degeneration. Sclerocorneal human trabecular meshwork cells (HTM cells. ScienceCell Research Laboratories, CA, USA) were grown in a nutritional medium containing 10% v/v fetal bovine serum, 2 mM L-glutamine, penicillin (100 IU/mL) at 37° C. in the presence of 5% v/v $CO_2$. Once cells were semi-confluent (80% covering of the plate surface), cells were collected by treatment with trypsin/EDTA and distributed in multiwell microplates at a density of $7\times10^3$ cells/well. Cells at 80% confluence were pre-treated for 30 minutes with 50 μL of eye drops with different polyphenolic concentration (0.15% *Perilla frutescens* extract in 0.25% sodium hyaluronate (high eye drops) compared with a 0.10% *Perilla frutescens* extract in 0.25% sodium hyaluronate (standard eye drops)).

After this time elapsed, $H_2O_2$ (200 μM) was added for five minutes.

Overall, the following treatments were performed:
1) Untreated control;
2) High eye drops or std eye drops (50 μL per well);
3) 50 μM $H_2O_2$ for 10 minutes;
4) Nanoparticle high eye drops or std eye drops (50 μL per well) (high eye drops+NP or std eye drops+NP);
5) Pre-treatment for 30 minutes with high eye drops or std eye drops+50 μM $H_2O_2$ for 10 minutes;
6) Pre-treatment for 30 minutes with high eye drops+NP or std eye drops+NP and 50 μM $H_2O_2$ for 10 minutes;
7) Co-treatment with high eye drops or std eye drops+50 μM $H_2O_2$ for 10 minutes;
8) Co-treatment with high eye drops+NP or std eye drops+NP and 50 μM $H_2O_2$ for 10 minutes;
9) Post-treatment with high eye drops or std eye drops and 50 μM $H_2O_2$ for 10 minutes;
10) Post-treatment with high eye drops+NP or standard eye drops+NP+50 μM $H_2O_2$ for 10 minutes.

Figure 1:
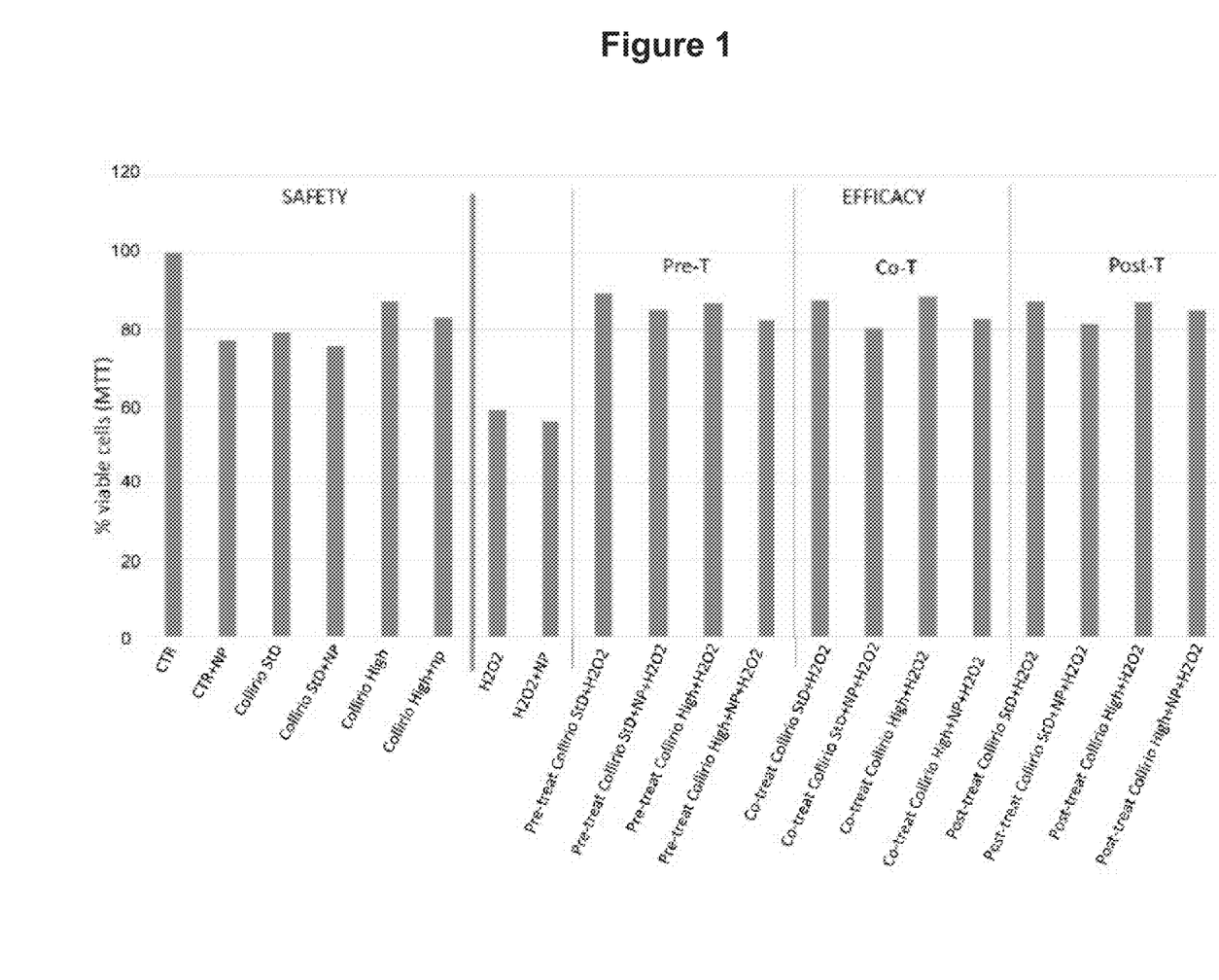
FIG. 1 represents a plot of the evaluation of cellular viability and genotoxic damage of cellular lines of human sclerocorneal trabecular meshwork (hereinafter also referred as HMT cells) variously treated or not treated with standard eye drops (or std eye drops), high eye drops, $H_2O_2$, nanoparticle eye drops or combinations thereof.

At the end of the treatment, the culture medium was removed, and cell viability and genotoxic damage were evaluated. The results of said tests are reported in the plot in FIG. 1.

In particular, cell viability was assessed using the metabolization test of 3-(4,5-dimethyithiazol-2-yl)-2,5-diphenyltetrazolium bromide (MTT). MTT is metabolized in mitochondria of viable cells in pigmented metabolites able to adsorb light at a length of 570 nm. Therefore, this test evaluates cell viability in terms of mitochondrial functionality and for that very reason was chosen, given the pathogenic importance that mitochondrial damage plays in the course of glaucoma. An MTT solution (Sigma Chemical Company (St. Luis, Mo., USA) (5 mg/mL MTT in PBS) was added to wells containing HTM cells and the mixture was incubated at 37° C. for 3 hours. A blank sample devoid of cells was included to subtract the background signal. The absorbance at 570 nm was determined in each of the assayed experimental conditions using a multi-plate microreader (Multiskan FC, Thermo Fisher Scientific, Shangai, China). 5 experiments repeated for each experimental condition were performed. The absorbance value in untreated control samples was reported as 100% viability and to this parameter the values recorded in the others experimental conditions were referred. The results were analysed by ANOVA using the Statview statistic software.

The results indicate that the eye drops in the two concentrations (std eye drops and high eye drops) do not negatively affect cell viability and are therefore safe. This characteristic is important because HTM cells are particularly sensitive to the side effects of ophthalmic eye drops.

A substantial cytopathic effect instead is shown by $H_2O_2$. This result is in line with the demonstrated high sensitivity of HTM cells to the oxidative damage.

The pre-treatment with std eye drops has been effective at reducing, in a statistically significant way (P<0.001), the cytopathic damage bringing it at values similar to the control.

This protective effect was found to be present also in case of co-treatment even though in a less relevant way (P<0.05). Conversely, the high eye drops have proven to be effective at decreasing the cytopathic damage when used in co- and post-treatment compared to the pre-treatment.

These results indicate how the protective mechanisms of eye drops are mainly due to the inducement of phase II protective metabolic systems at intra-cellular level, a mechanism requiring some time prior to be actually activated. The protective effect in co-treatment is due to direct scavenging by antioxidant compounds of reactive oxygen species and therefore does not require activation times.

In the pre-treatment mode, both mechanisms take place thus allowing to express the maximum protective efficacy against oxidative damage induced in HTM cells. These considerations are proven by the microscopic morphologic aspect of HTM cells in the different conditions of treatment.

In particular it has been observed that HMT cells show an elongated shape and are able to absorb the light (grey colour) in the control and in the treatment with the std eye drops only. This situation indicates a good cell viability and a good functionality of these endothelial cells which remain attached to the substrate. In the treatment with $H_2O_2$, cells take a rounded shape, separate from the substrate and reflect the light (white translucent colour). This situation indicates a severe structural and functional impairment of the cells with impaired viability.

In the pre-treatment with std eye drops, cells lose only in part their elongated shape but maintain the adhesion to the substrate and continue to absorb the light (grey colour).

This situation indicates that, despite a certain cellular suffering, HMT maintain their functional characteristics of endothelial cells. In the co-treatment instead, a certain number of translucent and rounded cells is observed, even though in a much lower amount than in the treatment with $H_2O_2$ only. This result indicate that the co-treatment is less effective than the pre-treatment at protecting HTM cells from oxidative damage contrary to what happens with the high eye drops.

Genotoxic Damage (Comet Test)

Figure 2:
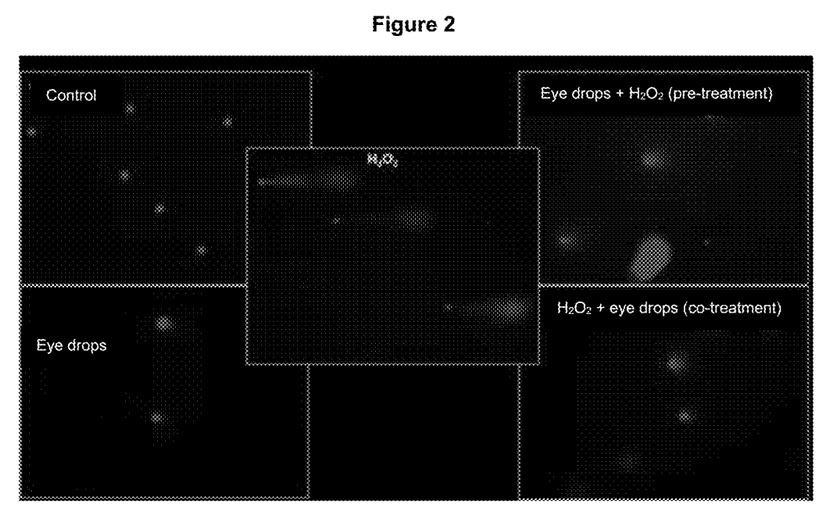
FIG. 2 represents images analysed at a magnification of 400 by fluorescence microscope (Leica DMI 4000B) obtained by means of Leica DFC310FX digital camera of HTM cells subjected to comet test for the assessment of genotoxic damage.

For the assessment of genotoxic damage, the comet test was used. Said test evaluates by alkaline gel electrophoresis of DNA the presence of fragile and apurinic sites resulting from the formation of oxidative lesions. The results obtained from the comet test are reported in FIG. 2. In particular, the aspect of DNA fragmentation acquired by the comet test in HTM cells was evaluated. HTM cells were resuspended in 75 µL of 0.5% p/v low melting agarose, distributed on a microscope slide covered with normal melting agarose and covered with a cover-slip. Agarose was solidified by cooling it at 4° C. The slide is then immersed in a lysis solution (2.4M $NaCl_2$, 100 mM $Na_2EDTA$, 10 mM Tris, pH 10, 1% Tritox X-100, 10% DMSO) for 1 hour at 4° C. The slides were then rinsed for 40 minutes in alkaline solution (0.3 M NaOH, 1 mM EDTA, pH 13) and placed in an apparatus for microelectrophoresis. The electrophoretic run was carried out for 30 minutes at 25 V (0.66 V/cm) with 300 mA intensity. After neutralization with neutral buffer (0.4 M tris-HCl, pH 7.5), the slides were dehydrated with absolute ethanol, dried and the nuclear DNA coloured with ethidium bromide (2 µg/mL). The images were then analysed at 400 magnifications by fluorescence microscope (Leica DMI 4000B) equipped with digital camera (Leica DFC 310 FX). For each slide a minimum of 100 nuclei were analysed by CASP imaging analysis system (Comet assay software project, http://www.casp.sourceforge.net). Single-strand and double-strand breaks were quantified in terms of "tail moment", which is the product of the comet tail length multiplied by the total DNA fraction in the tail. Tail moment is considered a reliable indicator of DNA damage as it takes into account both the distance of DNA electrophoretic migration and the amount of fragmented DNA contained in the tail. The significance of differences among the various treatments was determined by ANOVA test.

DNA seems free from fragmentation and not able to migrate in the electrophoretic run both in the control and in the cells treated with eye drops only, as demonstrated by the roundish aspect of the nuclei, their good migration and the lack of halos and tails.

Vice versa, in the treatment with $H_2O_2$, nuclei are massively dissolved with evident diffusion of the fragmented DNA during the electrophoretic run. This situation determines the formation of comets characterized by a very small nucleus and very elongated massive tail. DNA fragmentation is effectively attenuated by eye drops both in the pre- and co-treatment. In fact, in both these experimental situations, nuclei become well visible even if with a certain margining loss. However, the noticeable tails of fragmented DNA which do not appear in the pre-treatment are absent.

These results indicate how the employed std eye drops does not induce any DNA damage in HTM cells, also very sensitive to this kind of damage characteristically induced in them by some ocular eye drops in particular in the presence of preservatives. The std eye drops is effective in preventing the effects of DNA fragmentation induced by oxidative damage with higher efficacy in the pre-treatment mode with respect to the co-treatment one, contrary to what happens with the high eye drops.

Bioavailability Study

Eye drop bioavailability was evaluated by administering either the std eye drops or high eye drops as such and after inclusion in lipid nanoparticles as reported in the previous example.

These particles have the following characteristics: (1) superficial cationic groups to effectively bind the negatively charged cellular membranes; (2) ability to bind and carry hydrophobic drugs in the lipid interface (Nanoparticelle di Yun Wu, Nanoscale Science and Engineering Center of Affordable Nano-engineering of Polymeric Biomedical Devices, The Ohio State University, 174 West 18th Avenue, Room 1012, Columbus, Ohio 43210, United States).

The lipid nanoparticles were prepared as described in *Carcinogenesis*, 36(3):368-77 (2015) (supra).

Figure 3:
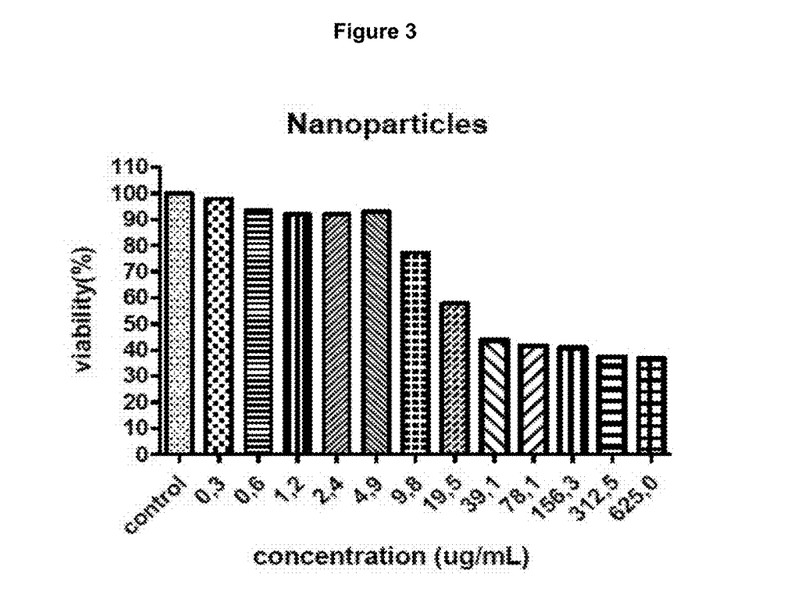
FIG. 3 represents a plot of the evaluation of cell viability (MTT) which verifies the effect of different concentrations of lipid nanoparticles at increasing concentrations.

An MTT assay of cellular viability was preliminary carried out to verify the effect of different concentrations of nanoparticles on HTM cells. The results are reported in FIG. 3.

Figure 4:
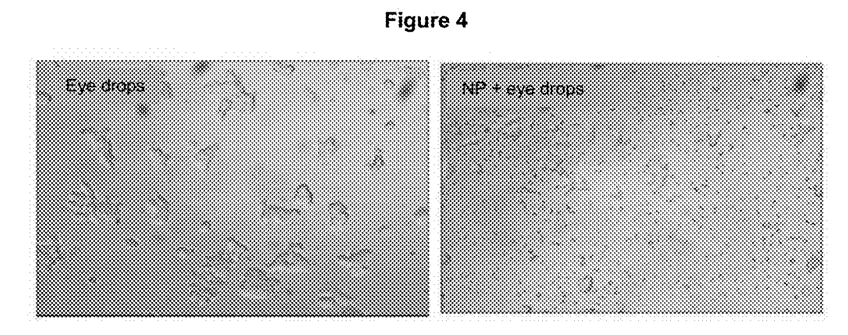
FIG. 4 represents two images of microscopic evaluation of HTM cells morphology in the presence of non-nanoparticle eye drops (left image) with respect to nanoparticle eye drops (right image) according to the present invention.
Figure 5:
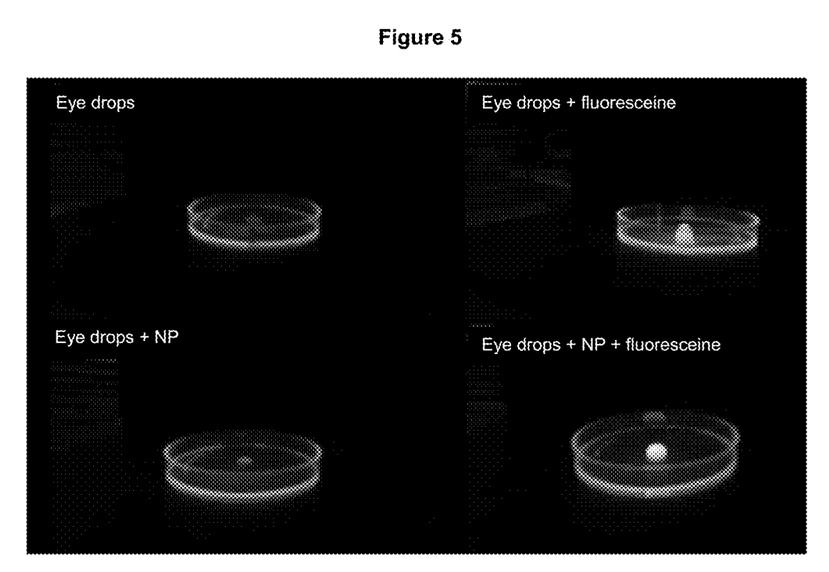
FIG. 5 represents an image obtained by a slit lamp (or biomicroscope) which highlights, using a fluorescent marker, the intraocular pharmacokinetic of a std eye drops with respect to a std eye drops with nanoparticles according to the present invention.
Figure 6:
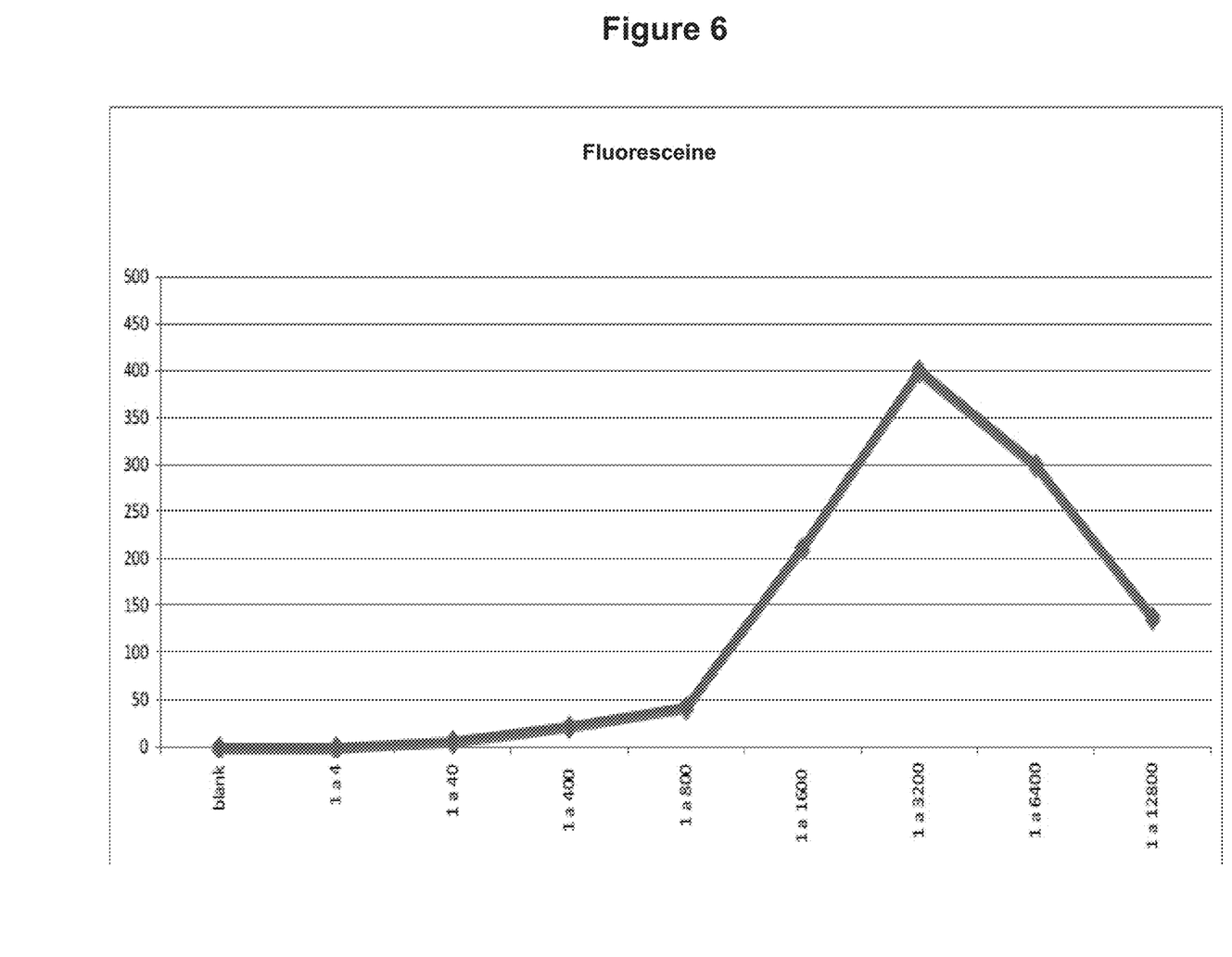
FIG. 6 is a plot highlighting the most suited dilution of fluoresceine to obtain the maximum efficacy of fluorescence.

In particular a microscopic evaluation of the HTM cells morphology in the presence of eye drops (left image) or nanoparticle eye drops (right image) was carried out. The lipid nanoparticles were aggregated by denaturation with DMSO in order to make the aggregates visible in optical microscopy.

In Vitro and In Vivo Bioavailability Tests.

The bioavailability was tested on whole ox eye (in vitro test) and on rabbit eyes (test in vivo) by applying the eye drops on the anterior corneal surface. A fluorescent tracer (fluoresceine) was added to the eye drops to follow the intraocular pharmacokinetics thereof.

The transcorneal distribution of the std eye drops was evaluated by a slit lamp with determination of the fluorescence on both sides of the corneal membrane.

A fluorescent tracer was added to the eye drops in order to follow the intraocular pharmacokinetics thereof. The selected fluorescent tracer is 5% fluorescein sodium; this choice is justified by the clinical use of said compound for the treatment and the study of retinal diseases such as, for example, diabetic retinopathy and retina degenerations.

The whole ox eye was treated applying on the anterior corneal surface a solution of std eye drops and fluoresceine (1 g/5 mL-5%), allowed to act for 30 minutes. At the end of the prescribed time, its adsorption through the anterior chamber was assessed using a slit lamp.

The std eye drops was administered as such or after inclusion in lipid nanoparticles incubating it at 37° C. for 30 minutes, as previously described.

Figure 9:
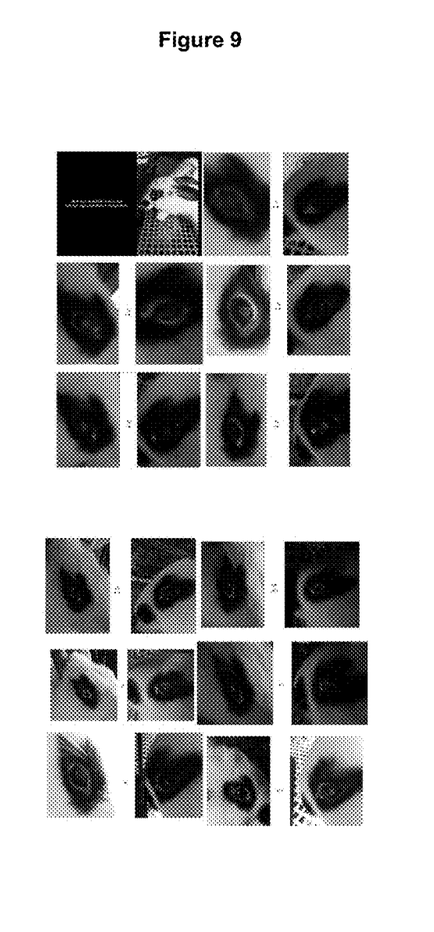
FIG. 9 represents imagines of rabbit eyes treated with high eye drops (right eye) and nanoparticle high eye drops (left eye) according to the present invention.

The fluoresceine was employed at the most suited dilution to obtain the maximum fluorescence efficacy, as calculated according to the curve reported in FIG. 9.

After the treatment, the fluid contained in the anterior chamber was collected and subjected to spectrofluorimetric analysis for the quantification of the tracer able to cross the corneal membrane.

For the analysis, a F3000 spectrofluorometer (Hitachi, Tokyo, Japan) calibrated on specific fluorescence characteristics of fluoresceine (excitation 500 nm, emission 561 nm) was used.

The samples were prepared according to the following conditions:
1. Blank (1 mL of saline solution)
2. Non fluoresceinated std eye drops (500 μL of eye drops+500 μL of saline solution)
3. Positive std control (200 μL of fluoresceine+800 μL of saline solution)
4. Fluoresceinated std eye drops (200 μL of fluoresceine+500 μL of eye drops+300 μL of saline solution)
5. Fluoresceinated nanoparticle std eye drops (200 μL of fluoresceine+500 μL of eye drops pre-incubated in NP+300 μL of saline solution).

Then the corneal permeabilization test was performed on ox eye. An example of the apposition of eye drops on the eye and of the transcorneal penetration thereof examined under white light by slit lamp is shown in FIG. 7.

Figure 7:
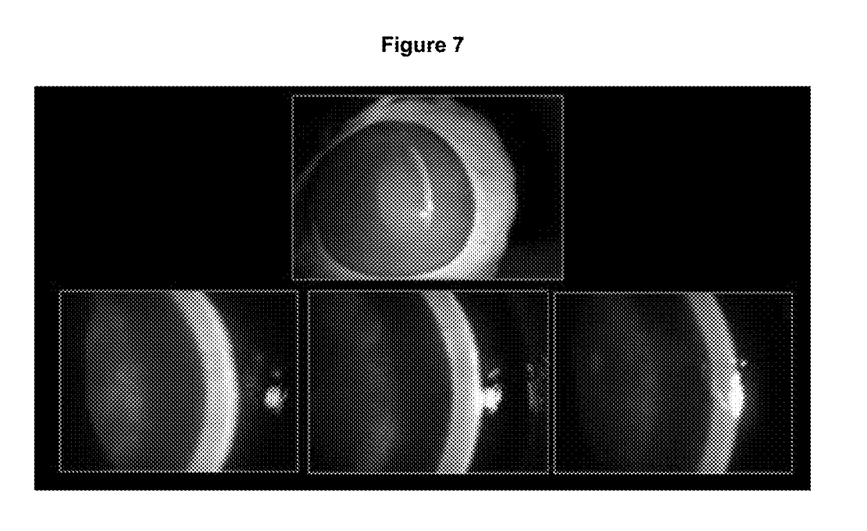
FIG. 7 shows images of bovine eye with application of fluoresceinated standard eye drops (below) compared with bovine eye as such (above).

The upper image of FIG. 7 shows the bovine eye while the bottom images are of bovine eye with apposition of fluoresceinated standard eye drops. In particular in the bottom images the eye is examined under slit lamp. The fluoresceinated eye drops is visible as white aggregate under normal light slit lamp. Its chronological transcorneal kinetic distribution is reported from left to right every 10 minutes. At 30 minutes (last image at the bottom right) is detectable the presence of eye drops beyond of corneal membrane.

The ability of the std eye drops, both as such and in nanoparticle form, to pass the corneal membrane was thus determined by analysis del fluorescent track present in the fluid in the anterior chamber 30 minutes after the application of the preparation on the anterior corneal surface.

Figure 8:
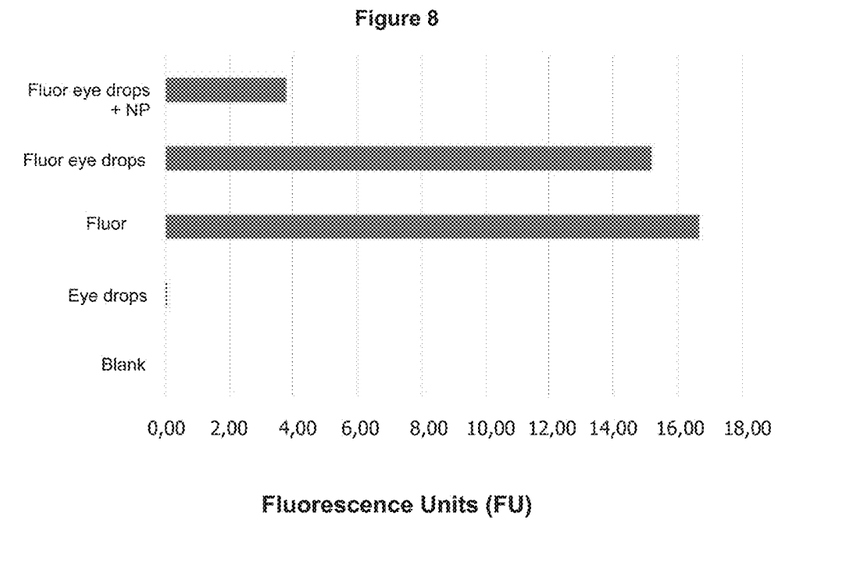
FIG. 8 is a plot showing the levels of fluoresceine expressed in FU (Fluorescence Units) in the anterior chamber of the eye with std eye drops and nanoparticle std eye drops according to the present invention.

The obtained results indicate that no unspecific fluorescence was detected in samples not treated with fluorochrome (Blank, eye drops). A conspicuous and specific positive signal was detected in the positive control consisting of fluoresceine (Fluor). The std eye drops labelled with fluorochrome was found in the fluid of the anterior chamber in a quantitatively significant manner (Fluor eye drops). The inclusion of the std eye drops in the nanoparticles slowed down its capacity to cross the corneal membrane (Fluor std eye drops+NP) see FIG. 8, increasing the permanence of the drug at corneal level and thus reducing its elimination and increasing the local bioavailability of the active ingredients.

The evaluation of the nanoparticle high eye drops was carried out through in vivo experiments on rabbit showing a persistence at ocular surface level of 16 hours compared to the non-nanoparticle formulation (see FIG. 9).

These studies demonstrated that nanoparticle ophthalmic compositions comprising a *Perilla frutescens* extract in an amount equal or higher to 0.10%, hyaluronic acid or a salt thereof in an amount equal or higher to 0.10% according to the present invention:
have protective efficacy in all the tested conditions;
the std eye drops is much more efficient in pre- and co-treatment whereas the high eye drops are much more efficient when administered in co- and post-treatment;
the nanoparticle formulation does not cause toxicity (as demonstrated by the effect on MMT);
the nanoparticle formulation does not alter the tolerability but increases the persistence time of the eye drops on the corneal surface. This was demonstrated by in vivo experiments.

The invention claimed is:

1. An ophthalmic composition consisting of:
0.1% to 0.15% by weight of *Perilla frutescens* extract,
at least about 0.1% by weight of sodium hyaluronate,
sodium chloride,
sodium phosphate monobasic monohydrate,
sodium phosphate dibasic anhydrous,
water, and
liposomes,
wherein the *Perilla frutescens* extract has a content of polyphenols of at least 2.5% by weight of the total weight of the extract,
wherein the *Perilla frutescens* extract, sodium hyaluronate, sodium chloride, sodium phosphate monobasic monohydrate, sodium phosphate dibasic anhydrous and water form an aqueous sterile solution,
wherein said aqueous sterile solution is included in the liposomes and wherein the liposomes consist of a lipid mixture of 1,2-di-O-octadecenyl-3-trimethylammonium propane (chloride salt):cholesterol:D-alpha-tocopheryl polyethylene glycol 1000 succinate at a molar ratio of 49.5:49.5:1, ethanol and N-2-hydroxyethylpiperazine-N'-2-ethanesulfonic acid buffer (pH 7.4).

2. An ophthalmic composition according to claim 1 wherein the ophthalmic composition is a sterile liquid formulation.

3. An ophthalmic composition of claim 2, wherein the sterile liquid formulation is selected from the group consisting of eye drops, semi-solid formulations, creams and gels.

4. An ophthalmic composition according to claim 3 wherein the sterile liquid formulation is in the form of eye drops.

5. An ophthalmic composition according to claim 1 wherein the sodium hyaluronate is present in the amount of about 0.1% to about 0.5% by weight with respect of the total weight of the ophthalmic composition.

6. An ophthalmic composition according to claim 5 wherein the sodium hyaluronate is present in the amount of about 0.25% by weight with respect to the total weight of the ophthalmic composition.

7. An ophthalmic composition according to claim 1 wherein the mean diameter of the liposome is between about 50 and about 1000 nm.

8. An ophthalmic composition according to claim 7 wherein the mean diameter of the liposome is between about 100 and about 500 nm.

9. An ophthalmic composition according to claim 8 wherein the mean diameter of the liposome is between about 30 and about 60 nm.

10. An ophthalmic composition according to claim 8 wherein the mean diameter of the liposome is between about 45 and about 50 nm.

11. An ophthalmic composition of claim 1 wherein the *Perilla frutescens* extract is present in the amount of 0.15% by weight and the sodium hyaluronate is present in the amount of 0.25% by weight with respect to the total weight of the ophthalmic composition.

12. A sterile liquid formulation, in the form of eye drops, according to claim 3 having a viscosity between about 10 cSt and about 40 cSt.

13. A method of treating an ocular disorder or disease in a patient in need thereof, comprising administering an effective amount of a composition of claim 1 to the affected area of the eye of said patient.

14. A method for the treatment of an ocular disorder or disease selected from the group consisting of tear dysfunction syndrome, dry eye, diabetic retinopathy and glaucoma, comprising administering an effective amount of a composition of claim 1 to the affected ocular region of a patient in need thereof.

15. A method according to claim 14, wherein the ocular disorder is tear dysfunction syndrome.

\* \* \* \* \*